United States Patent [19]

DeVincenzo et al.

[11] Patent Number: 5,562,445
[45] Date of Patent: Oct. 8, 1996

[54] RESILIENTLY EXPANDABLE ORTHODONTIC DEVICE

[76] Inventors: John DeVincenzo, 1312 Garden St.; Steven Prins, 826 Alyssum Ct., both of San Luis Obispo, Calif. 93401

[21] Appl. No.: 492,251

[22] Filed: Jun. 22, 1995

[51] Int. Cl.[6] ................................................. A61C 3/00
[52] U.S. Cl. .................................... 433/19; 433/18
[58] Field of Search ............................ 433/18, 19, 24

[56] References Cited

U.S. PATENT DOCUMENTS

| | | | |
|---|---|---|---|
| 3,618,214 | 11/1971 | Armstrong | 433/19 |
| 3,690,003 | 9/1972 | Gerber | 433/19 X |
| 3,798,773 | 3/1974 | Northcutt | 433/19 |
| 4,462,800 | 7/1984 | Jones | 433/19 |
| 4,571,178 | 2/1986 | Rosenberg | 433/18 |
| 4,795,342 | 1/1989 | Jones | 433/19 |
| 5,074,784 | 12/1991 | Sterret et al. | 433/19 X |
| 5,183,388 | 2/1993 | Kumar | 433/19 |

Primary Examiner—Nicholas D. Lucchesi
Attorney, Agent, or Firm—James B. Middleton

[57] ABSTRACT

An orthodontic appliance has a cylinder with a spring urged plunger therein. The spring is compressed when the plunger is moved into the cylinder; and, one end of the cylinder and the extending end of the plunger are attached between the teeth to be moved. The attachments to the teeth allow universal motion so the law is free to move in all directions anatomically possible. To extend between the upper and lower teeth, the cylinder can be slidable within a second cylinder. The second cylinder allows greater extension of the appliance while maintaining the integrity of the appliance.

14 Claims, 2 Drawing Sheets

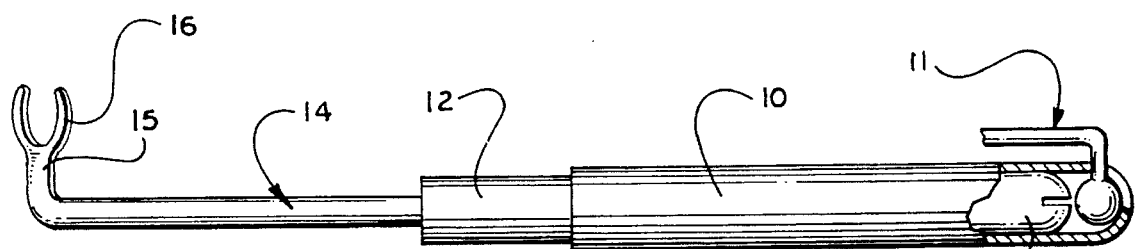
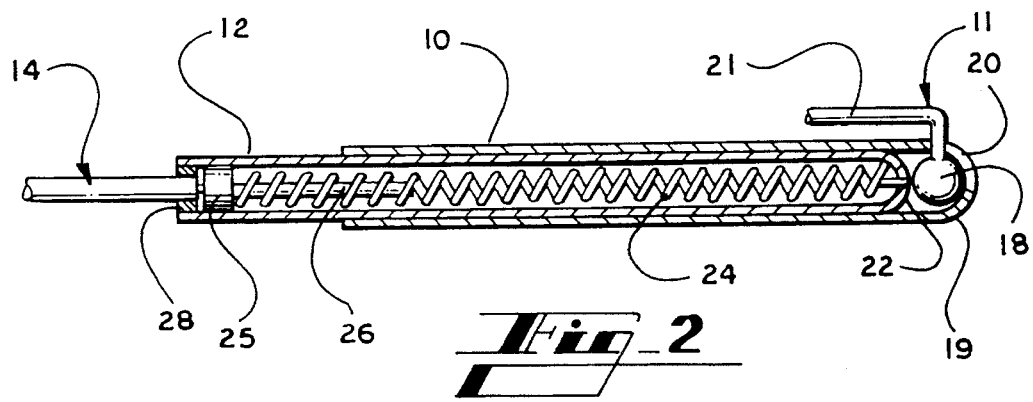
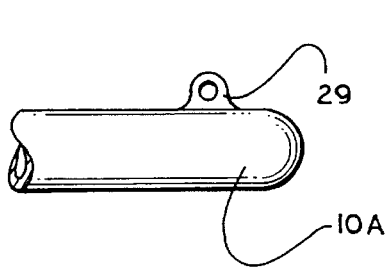
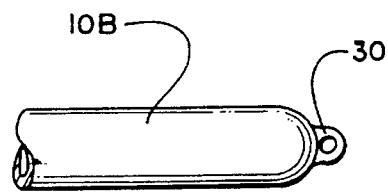
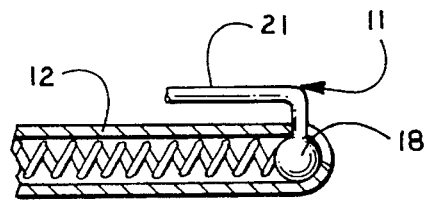

RESILIENTLY EXPANDABLE ORTHODONTIC DEVICE

BACKGROUND OF THE INVENTION

1. Field of the Invention

This invention relates generally to orthodontic appliances, and is more particularly concerning with a resiliently expandable arrangement that normally applies a force between the upper and lower teeth but is sufficiently extendible to allow free movement of the mandible.

2. Discussion of the Prior Art

It is common in orthodontics to utilize appliances that exert a force between the maxillary and the mandibular dentitions in order to induce orthopedic and/or orthodontic correction. Early forms of such appliances comprise simply coil springs connected between the maxilla and the mandible. While these springs will exert the force needed, they are uncomfortable for the patients in that the cheek Gets pinched in the coils of the spring, and food and the like accumulates in the springs. Additionally, they have been of very short life because of rapid and frequent breakage while severely restricting the movement of the mandible.

One solution to the above mentioned problems is to cover the springs as shown in the patent to Armstrong, U.S. Pat. No. 3,618,214. While such a covering diminishes the problems, it does not affect the problem of limited mandibular motion. More recent efforts at solving the problems are shown in patents U.S. Pat. No. 4,708,646 to Jasper and U.S. Pat. No. 4,795,342, to Jones. The Jones device has a spring enclosed within a cylinder, but still allows very limited motion. The Jasper device has a spring encased in an elastic material, and provides somewhat loose connections to give some freedom, but still does not allow full motion of the mandible.

SUMMARY OF THE INVENTION

The present invention provides an orthodontic appliance having spring means enclosed within a cylindrical housing. In its relaxed state the device is fully extended, so the device is compressed for installation to yield the desired force. Each end of the device is arranged for swivel mounting to the teeth to allow freedom of movement of the mandible in all normal directions. The cylinder housing the spring means may be slidably received within another cylindrical housing to expand the range of extension of the device. Thus, the mandible can be opened to the maximum extent anatomically possible, and the device of the present invention will allow such movement, and will not be separated or damaged by such movement. Additionally, unlimited lateral excursions are obtainable with only the present device.

BRIEF DESCRIPTION OF THE DRAWINGS

These and other features and advantages of the present invention will become apparent from consideration of the accompanying drawings in which:

FIG. 1 is a side elevational view, partially in cross-section, showing an orthodontic appliance made in accordance with the present invention;

FIG. 2 is a longitudinal cross-sectional view of the device shown in FIG. 1, one end being broken away;

FIGS. 3 and 4 are fragmentary details showing alternate connecting means for the device of FIG. 1;

FIG. 4A is a fragmentary cross-sectional view showing another modified form of the invention; and, FIGS. 5 and 6 are side elevational views showing the device of FIG. 1 installed on orthodontic appliances, FIG. 5 showing the mandible in closed position and FIG. 6 showing the mandible in fully open position.

DETAILED DESCRIPTION OF THE EMBODIMENTS

Figure 5:
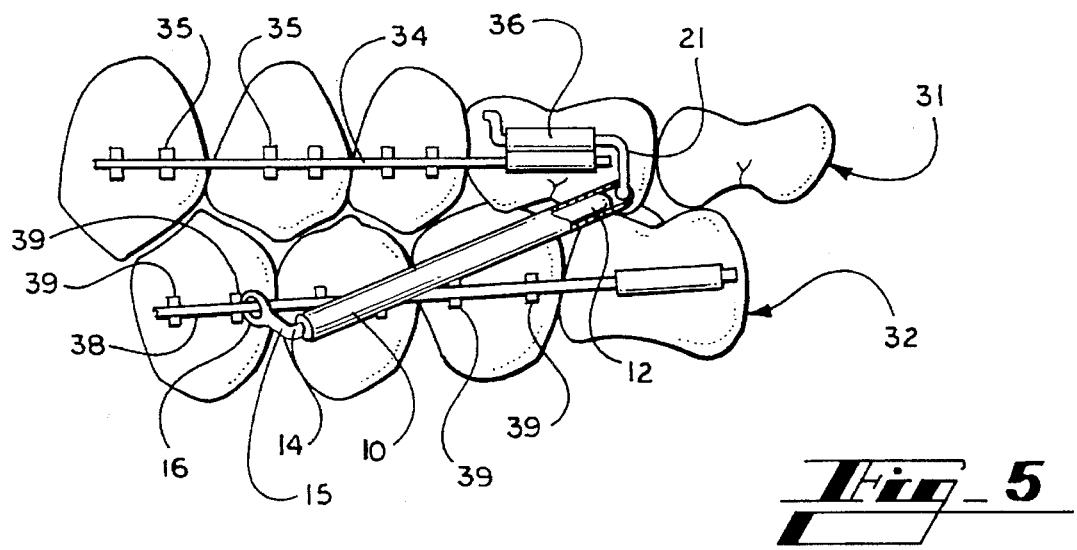

Referring now more particularly to the drawings, and to those embodiments of the invention here presented by way of illustration, FIG. 1 shows an orthodontic appliance made in accordance with the present invention, the device including an outer barrel 10 having an attaching means 11 at one end thereof. An inner barrel 12 is slidably received in the outer barrel 10 and, as will be better understood hereinafter, there is no permanent connection between the outer barrel 10 and the inner barrel 12.

The inner barrel 12 receives a plunger 14 therein. As will be discussed in more detail hereafter, the plunger 14 is shown in its most extended position in FIG. 1. The plunger 14 has a bent end 15 that is angulated differently for the left and right sides, and includes attaching means 16. The angulation depicted at 15 permits sliding without binding on the arch wire when the mouth is open.

With attention to FIGS. 1 and 2, the construction of the device can be understood in more detail. The attaching means 11 on the outer barrel 10 includes a ball 18 within a crimped, rounded end 19 of the outer barrel 10. A slot 20 is provided for the connecting arm 21 to extend from the barrel 10. Those skilled in the art will understand that the connecting arm 21 may be of any desired length, and shape, to be fixed to various orthodontic appliances for support. The ball and socket arrangement provided by the ball 18 in the rounded end 19 allows free movement of the barrel 10 with respect to the connecting arm 21.

The attaching means 16 on the plunger 14 is here shown as a crimpable clamp. The attaching means is simply a bifurcated member that can be closed around an arch wire or other appliance. It is contemplated that the remaining opening in the attaching means 16 will be large enough that there will be "play" in the connection, sufficient to allow free movement between the plunger and the patient's teeth.

The inner barrel 12 of the present invention has a crimped end 22 against which one end of a spring 24 rests. The opposite end of the spring 24 rests against a stop 25 which is fixed to a guide pin 26, the guide pin 26 being a coaxial extension of the plunger 14. There is a check stop 28 in the open end of the inner barrel 12. The opening in the check stop 28 is sufficient to allow entry of the plunger 14, but the stop 25 cannot pass the check stop 28.

With the above description in mind, it will be understood that the plunger 14 is held in its projected position by action of the spring 24 between the stop 25 and the barrel end 22. The plunger 14 can be urged into the inner barrel 12 by overcoming the spring tension. The inner barrel 12 is slidable within the outer barrel 10, and there is no restriction on such movement except the closed end 19 of the barrel 10. Also, since both barrels 10 and 12 are cylindrical, the two cylinders can rotate relative to each other.

The attaching means 11 shown in FIGS. 1 and 2 is the preferred embodiment of the invention, but other mechanical arrangements can be used. By way of example, FIG. 3 shows an outer barrel 10A having a tab 29 on the side thereof. The tab 29 has a hole therein for connection to an orthodontic appliance. It is contemplated that the connection would be rather loose to allow the desired freedom of movement. FIG. 4 shows another variation, the barrel 10B having a tab 30 at its end. This tab would be used the same as the tab 29, and no further discussion is thought to be necessary.

Those skilled in the art will realize that, in some situations, the additional extension provided by the inner and outer cylinders 10 and 12 may not be required. In these instances, the inner cylinder 12 can be used alone. Thus, FIG. 4A illustrates the crimped end of the inner cylinder with the ball-and-socket connections means. It will be understood that the plunger and its attaching means will be the same, and the only difference is that there will be no outer cylinder 10.

Figure 6:
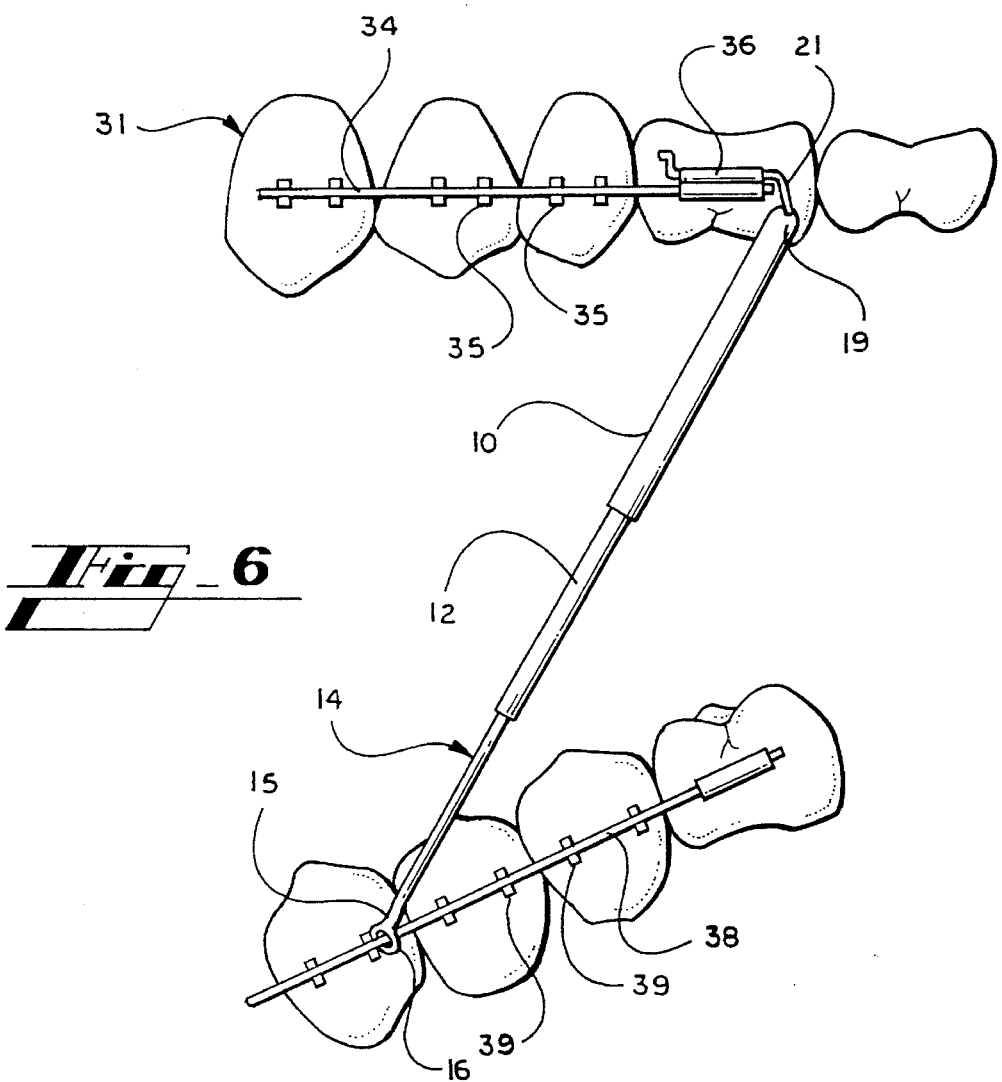

Attention is now directed to FIGS. 5 and 6 for a more detailed description of the use of the device of the present invention. FIG. 5 illustrates the maxillary teeth 31 and the mandible teeth 32, the maxillary teeth 31 being farther out (to the left in the drawing) than they ought to be.

An arch wire 34 is fixed to the maxillary teeth 31 by a plurality of brackets 35. The rear (right) end of the arch wire 34 has a coupling 36 fixed thereto, the coupling 36 receiving the connecting arm 21 of the attaching means 11. Similarly, an arch wire 38 is fixed to the mandible teeth 32 by a plurality of brackets 39. It will be seen that the crimpable clamp 16 has been closed around the arch wire 38 between brackets. It should also be noticed that the clamp 16 does not grip the arch wire 38 tightly, but has a large enough opening that the plunger 14 can move freely with respect to the arch wire 38, within certain limits.

It will be remembered that the spring 24 must be compressed for the plunger 14 to be within the inner cylinder 12 as illustrated in FIG. 5. As a result, it will be understood that there is a constant force exerted, the force tending to move the maxillary teeth 31 to the right as viewed in FIG. 4, and the mandible teeth 32 to the left. As the person's mouth is opened, the mandible pivoting down from the position shown, the spring 24 will continue to exert a force tending to move the teeth. Once the plunger 14 is fully extended, there will no longer be a force; but, when the mandible is again closed, the spring force will again be exerted.

FIG. 6 shows the mandibular teeth 32 in the position in which the mouth is as far open as anatomically possible. In this position of course the plunger 14 is fully extended from the inner cylinder 12. The important points, however, are that the device as a whole has not lost its integrity, and the mandible can be moved as much as is normally possible in any direction, and the device of the present invention will not hinder such motion.

The great extension of the device of the present invention is made possible, first, by the plunger 14 within the inner cylinder 12, and, second, by the inner cylinder's sliding within the outer cylinder 10. The universal motion of the mandible is then allowed by the ball-and-socket joint between the attaching arm 21 and the outer cylinder and the loose connection of the clamp 16 on the arch wire 38. Additionally, the fact that the inner cylinder 12 is freely rotatable within the outer cylinder 19 contributes to the free motion. It will of course be understood by those skilled in the art that other connection means can be used to attach the device of the present invention to the orthodontic appliances. The important feature is that motion be allowed between the device of the present invention and the appliances or the like that attach the device to the teeth.

While the illustrations in FIGS. 5 and 6 show the device of the present invention being used to move the mandibular teeth and jaw forward while moving the maxillary teeth and jaw backward, it will be observed that one can simply reverse the device, fixing the attaching means 11 towards the front of the maxillary teeth 31 and fixing the clamp 16 towards the back of the mandibular teeth, and the force exerted will be reversed. The person skilled in the art will devise numerous specific installations using the device of the present invention.

It will therefore be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

We claim:

1. An orthodontic appliance for exerting a force between a first point on a set of teeth and a second point on said set of teeth, said set of teeth including maxillary teeth and mandible teeth, said mandible teeth being universally movable with respect to said maxillary teeth, said appliance comprising a substantially rigid cylinder having a first end and a second end, a plunger having a first end and a second end, said plunger being at least partially within said cylinder, a coil spring within said cylinder, said coil spring engaging said first end of said plunger for urging said plunger from said cylinder, stop means for preventing separation of said plunger from said cylinder, first attaching means for attaching said first end of said cylinder to one of said points on a set of teeth, and second attaching means for attaching said second end of said plunger to the other of said points on a set of teeth, said first attaching means comprising a ball within said cylinder, said second attaching means comprising a crimpable clamp for loosely engaging said second point so that said first and second attaching means allow universal motion between said orthodontic appliance and said set of teeth.

2. An orthodontic appliance as claimed in claim 1, said plunger being rotatable with respect to said cylinder.

3. An orthodontic appliance as claimed in claim 1, and further including a guide pin extending from said plunger within said cylinder, said coil spring surrounding said guide pin.

4. An orthodontic appliance as claimed in claim 1, wherein said crimpable clamp extends at an angle from said plunger towards said set of teeth.

5. An orthodontic appliance for exerting a force between a first point on a mandible set of teeth and a second point on a maxillary set of teeth, said appliance comprising a first substantially rigid cylinder having a first end and a second end, a plunger having a first end and a second end, said plunger being at least partially within said first cylinder, spring means within said first cylinder, said spring means engaging said first end of said plunger and said first end of said first cylinder for urging said plunger from said first cylinder, a second substantially rigid cylinder slidably receiving said first cylinder therein with said second end of said first cylinder extending from said second end of said second cylinder, and first attaching means for attaching said first end of said second cylinder to one of said points, and second attaching means for attaching said second end of said plunger to the other of said points.

6. An orthodontic appliance as claimed in claim 5, wherein said spring means comprises a coil spring extending between said first end of said first cylinder and said first end of said plunger so that inward movement of said plunger compresses said coil spring.

7. An orthodontic appliance as claimed in claim 5, wherein said first and second attaching means allow universal motion between said orthodontic appliance and said set of teeth.

8. An orthodontic appliance as claimed in claim 7, wherein said first attaching means comprises a ball received within said first end of said second cylinder, said ball being rotatable for allowing motion between said orthodontic appliance and said set of teeth.

9. An orthodontic appliance as claimed in claim 7, wherein said second attaching means comprises a crimpable clamp for loosely engaging said second point on said set of teeth.

10. An orthodontic appliance as claimed in claim 9, wherein said crimpable clamp extends at an angle from said plunger towards said set of teeth.

11. An orthodontic appliance as claimed in claim 7, said plunger being rotatable with respect to said first cylinder, and said first cylinder being rotatable with respect to said second cylinder.

12. An orthodontic appliance as claimed in claim 11, and further including stop means for preventing separation of said plunger from said first cylinder.

13. An orthodontic appliance as claimed in claim 5, said first cylinder and said second cylinder being so dimensioned that said first cylinder is still partially received within said second cylinder when said mandible teeth are farthest removed from said maxillary teeth.

14. An orthodontic appliance as claimed in claim 5, and further including a guide pin extending from said plunger within said first cylinder, said spring means surrounding said guide pin.

* * * * *